United States Patent [19]

Dickey

[11] Patent Number: 4,548,803
[45] Date of Patent: * Oct. 22, 1985

[54] CONTINUOUS FLOW SEPARATION WITH MOVING BOUNDARY SORPTION

[75] Inventor: Leland C. Dickey, Omaha, Nebr.

[73] Assignee: InterNorth, Inc., Omaha, Nebr.

[*] Notice: The portion of the term of this patent subsequent to Oct. 22, 2002 has been disclaimed.

[21] Appl. No.: 638,283

[22] Filed: Aug. 6, 1984

Related U.S. Application Data

[63] Continuation-in-part of Ser. No. 561,899, Dec. 15, 1983.

[51] Int. Cl.[4] ................... B01D 15/02; B01D 15/08
[52] U.S. Cl. ........................... 423/659; 55/34;
55/67; 55/77; 55/181; 55/390; 210/656;
210/670; 210/671; 210/673; 210/198.2;
423/210; 435/70; 435/174; 435/183; 435/184;
435/287; 435/803
[58] Field of Search ................ 55/34, 77–79,
55/99, 181, 390, 67, 386, 656–659; 423/219,
659, 210 R, 210 S; 210/660, 670, 671, 676,
198.2, 198.3; 435/70, 174, 183, 184, 287, 803;
422/70

[56] References Cited

U.S. PATENT DOCUMENTS

| | | | |
|---|---|---|---|
| 2,222,828 | 11/1940 | Guthrie | 55/390 |
| 2,302,807 | 11/1942 | Shoeld | 55/390 |
| 2,639,000 | 5/1953 | Edwards | 184/4.6 |
| 2,678,132 | 5/1954 | Beard | 210/670 |
| 3,335,081 | 8/1967 | El-Nagger | 210/619 |
| 3,498,026 | 3/1970 | Messinger | 55/390 |
| 3,598,726 | 8/1971 | Welch | 210/619 |
| 3,757,492 | 5/1971 | Graff | 55/181 |
| 3,907,967 | 9/1975 | Filss | 423/210 S |
| 4,083,778 | 4/1978 | McGrew | 210/671 |
| 4,242,107 | 12/1980 | Jenkins | 55/390 |
| 4,292,054 | 9/1981 | Noack | 55/181 |
| 4,302,222 | 11/1981 | Miller | 55/390 |
| 4,324,564 | 4/1982 | Oliker | 55/20 |
| 4,348,290 | 9/1982 | Schipper | 210/783 |
| 4,351,650 | 9/1982 | Shinoda | 55/181 |
| 4,353,720 | 10/1982 | Margrat | 55/262 |
| 4,391,616 | 7/1983 | Imamura | 55/390 |
| 4,415,342 | 11/1983 | Foss | 55/96 |

FOREIGN PATENT DOCUMENTS

| | | | |
|---|---|---|---|
| 3102280 | 8/1982 | Fed. Rep. of Germany | 55/77 |
| 46-38241 | 12/1969 | Japan | 210/670 |
| 46-18547 | 5/1971 | Japan | 210/671 |
| 1339621 | 12/1973 | United Kingdom | 55/390 |

OTHER PUBLICATIONS

Perry's Chemical Engineers' Hand Book, McGraw Hill, Fourth Edition, 1969, 16–20, 16–24 and 16–25.

*Primary Examiner*—Ernest G. Therkorn
*Attorney, Agent, or Firm*—Donald F. Haas

[57] ABSTRACT

A continuous process for separating components of a fluid mixture is disclosed which comprises forming a sorption zone and a desorption zone, said sorption and desorption zones being separated by a boundary of a sorbent material which continuously moves back and forth between the sorption and desorption zones, causing a fluid mixture to flow into the sorption zone wherein the conditions are such to promote sorption of one of the components of the mixture by the sorbent material, and creating conditions in the desorption zone such that the sorbed component will be desorbed when the sorbent material containing the sorbed component moves into the desorption zone. There may be disposed between the sorption and desorption zones at least one roller and at least one moving belt or at least two moving belts. The process can also be used to form a mixture with content of the sorbable component controlled by the sorption/desorption cycle.

6 Claims, 4 Drawing Figures

CONTINUOUS FLOW SEPARATION WITH MOVING BOUNDARY SORPTION

REFERENCE TO RELATED APPLICATIONS

This application is a continuation-in-part of my application entitled "Continuous Flow Separation or Mixing with Moving Boundary Sorption", Ser. No. 561,899, filed Dec. 15, 1983. This application is currently pending before the Patent & Trademark Office. Reference is also made to copending allowed application Ser. No. 638,255.

BACKGROUND OF THE INVENTION

This invention relates to a continuous process for obtaining optimal separation of a fluid mixture by sorption. The method also relates to a process for preparing precise fluid mixtures where the metered component is mixed by moving boundary sorption.

In recent years, cyclic separation processes have received considerable attention. Such processes as pressure-swing adsorption, parametric pumping, and cycling zone adsorption, separate continuous or semi-continuous fluid feed streams by cycling a thermodynamic variable which affects the mass transfer of fluid components with a sorption media. The cycle is designed to alternately sorb and desorb components so the fluid components are separated and the media returns to its initial condition after the completion of a cycle. The feed and product streams can be rendered continuous by combining sorption units in parallel but each unit necessarily experiences discontinuous flow conditions so that the sorbing media can be altered by changing thermodynamic variables such as temperatures, pH, or pressure, for example, and so that the other product stream can be created thereby. The discontinuity of flow through or past the sorbing media creates inefficiency in the separations because of the mixing of fluid elements that have been exposed to the sorbing media under different conditions.

All practical separation techniques that occur with discontinuous flow result in product reservoir mixing. Since the feed mixture flows through the vessel during the sorption cycle of the cycling process, the sorbent will fill with the sorbed fluid component and the sorptivity will decrease. Thus, fluid entering the vessel early in the cycle is stripped of the sorbable constitutents to a greater extent than fluid entering late in the cycle. As a reult, the composition of the fluid emerging from the sorbent zone is continually changing. Such a system cannot be controlled as efficiently as a single condition, continuous, time invariant process because in the cyclic operation you must compromise between optimizing for the early portion of the sorption cycle and the later portion. The ideal situation where product flow streams are not mixed would require a prohibitively large number of separate reservoirs as well as a complicated flow management system.

It is an object of the present invention to provide a method for continuous flow separation or mixing which avoids the inefficiencies inherent in reservoir mixing. It is a further object of the present invention to provide a continuous method of flow separation or mixing wherein only a significant part of the seal between the sorption and desorption zones is the sorption media itself.

SUMMARY OF THE INVENTION

The present invention relates to a continuous process for separating components of a fluid mixture which comprises first forming at least one sorption zone and at least one desorption zone. The sorption and desorption zones are separated by a boundary of a sorbent material which continuously moves back and forth between the sorption and desorption zones. A fluid mixture is caused to flow into the sorption zone wherein the conditions are such to promote sorption of at least one of the components of the mixture by the sorbent material. Finally, conditions are created in the desorption zone such that the sorbed component will be desorbed when the sorbent material containing it moves into the desorption zone.

In a preferred embodiment of the present invention, there is disposed between the sorption and desorption zones, a rotating roller or rollers and a moving belt or belts, each of which may have the sorbent material at least on the surfaces thereof and which are in engagement so that the sorbent material forms the boundary between the sorption and desorption zones. More than one roller and more than one moving belt may be used and one or more of the rollers and one or more of the belts may contain the sorbent material. In another preferred embodiment of this invention, there is disposed between the sorption and desorption zones two or more moving belts which have the sorbent material at least on the surface thereof and which are in engagement so that the sorbent material forms the boundary between the sorption and desorption zones.

In another embodiment of the present invention, the desorbed component forms a part of a second fluid mixture which is present in the desorption zone. In such a situation, the desorption zone can be a reaction zone wherein the rate of reaction is controlled by the amount of desorbed component which enters the desorption zone.

DETAILED DESCRIPTION OF THE INVENTION

Figure 1:
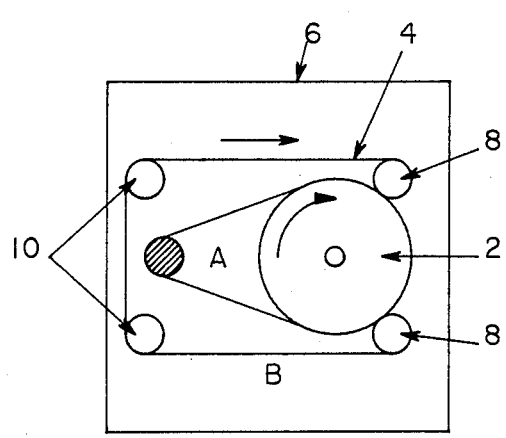
FIG. 1 is a cross section of a desorption apparatus illustrating the use of a large sorbent roller in combination with a moving belt to define the sorption and desorption zones.

As stages above, the process of the present invention provides a continuous method for separating components of a fluid mixture. The invention requires that separate chambers be connected by a rotatable sorbent barrier which will continuously alternate the sorbent face exposed to each chamber. The rotation rate will be varied to optimize separation in conjunction with the fluid stream throughput and the sorption/desorption conditions.

As stated above, a fluid mixture is caused to flow into the sorption zone wherein the conditions are such to promote sorption of one of the components of the mixture by the sorbent material. Then conditions are created in the desorption zone to promote the desorbing of the sorbed component when the sorbent material containing it moves into the desorption zone. Thermodynamic variables such as temperature and pressure can be used to influence the sorption and desorption of the component of the original fluid mixture. Other variables such as pH, concentration of other chemical species, or voltage can also be used to influence the sorption/desorption process. Examples of fluid separations which can be performed according to the method of the present invention are aqueous acetic acid, aqueous glucose and fructose, enzyme mixtures in aqueous solution, dipeptides in aqueous solution, and any gas mixture where one component or group of components can be selectively sorbed. Hydrogen and water can be readily removed from nonpolar gases such as power plant exhaust gases.

The process of the present invention can also be used to mix fluid components together. Mixing is accomplished in exactly the same manner as separation—the difference is only in which side of the process, sorption or desorption, is considered the product stream. The mixture mode is useful in preparing precise fluid mixtures where the metered component is carried into the desorption or product chamber by the sorbent material. The product chamber might in fact be a reaction chamber where the feed or the sorbent-carried reactant is rate controlling. An example of this is partial oxidation of hydrocarbons in which oxygen is transported from an air chamber to a reaction chamber by a sorbent material. In this case, both chambers could be at high pressure because the absorbed oxygen would be desorbed by reaction rather than partial pressure reduction as in the case of other fluid separations. The pressure of the two chambers should be nearly equal to minimize gas leakage or pumping by the moving elements.

For the purposes of this invention sorbent materials are generally of four types:

1. Solids which can absorb gases in the bulk of the material. For example FeTi, LaNi$_5$, and the other so-called metal hydrides can absorb hydrogen. Solids which a high specific surface such as Fuller's earths, bauxite, alumina, gas adsorbent carbon, silica gel and zeolites (aluminosilicates) can be used. In some of these latter examples considerable temperature elevation is required to regenerate the adsorptivity. This might necessitate some modification of the apparatus design so that the desorption chambers can withstand the heat.

2. Porous insoluble solids containing absorbent liquids, such as carboxy-methyl cellulose, (CMC)/water, or saponified starch-g-polyacrylonitrile, (HSPAN)/water, can be used. In either case the water is strongly bound to the solid but is still as absorptive as pure water. Other polar solvents or aqueous solutions could be used with these solids (CMC or HSPAN) but is likely that modification of the constituent solid would be the preferred way to optimize a particular gas absorption application. Generally, the polarity of the solid should match that of the chosen absorbent liquid to maximize liquid content in the sorbent combination. Consequently, various hydrocarbon-swellable polyolefins would provide suitable mechanical support for alkanes or other nonpolar liquids.

3. Gels formed from solvents and soluble solids such as polymers of soluble monomers can also be used. The distinction from (2) is that in this case the solid does not provide any structural form and therefore the gel can be applied as a coating to an existing solid or possibly cast into appropriate form. Examples are protein/water, cellulose acetate/water, ABS polymers/ketones, and polystyrene/aromatic solvents.

4. Solids formed from a combination of fluids that solidify under conditions in the sorption chamber, especially where one of the fluids is the sorbed component, can be used. This is the most complicated case from the standpoint of designing a process in which the sorption phase seals the chambers. However, it is the only one where elasticity of the sorbent will not be necessary to achieve a tight fit between the moving elements. Examples would be hydrate formation or reversible polymerization of a fluid monomer being removed from a mixture with nonpolymerizable components. It is possible that if one of the combining components is more or less permanently fixed to the moving element, e.g. water in the case of hydrate formulation, it could be supported in or with a solid material such as cases (2) and (3) above.

It is very important to the present invention that the sorbent material provides the seal which separates the sorption zone from the desorption zone. In order to accomplish this, the sorbent material may be deformable so that it can provide an acceptable seal. The separation between the sorption and desorption zones can be provided by a combination of one or more rollers and one or more moving belts and also by the combination of two or more moving belts without any rollers. In the first case, either the rollers or the belts, or both, may have the sorbent material at least on the surfaces thereof and in the latter case, one, part, or all of the belts may have the sorbent material thereon. In fact, it is possible to use more than one type of sorbent so that more than one selectivity for the sorbed component is possible with the apparatus of this invention. The important aspect of all of the embodiments of this invention is that the rollers or belts be in engagement so that the sorbent material forms a boundary seal between the sorption and desorption zones.

FIG. 1 illustrates one particular embodiment of the present invention wherein a large roller 2 which contains or is coated with the sorbent material is used in combination with a moving belt 4 to define a desorption zone A. The belt 4 and the outer housing 6 define sorption zone B. Rollers 8 maintain the belt 4 in engagement with the large roller 2 and guide rollers 10 assist in positioning the belt 4 properly.

Figure 2:
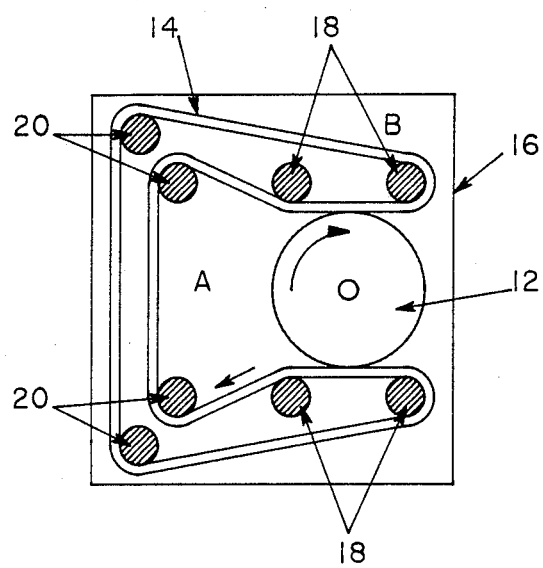
FIG. 2 is a cross section of an apparatus wherein a moving belt coated with the sorbent material is used in combination with a large roller.

FIG. 2 illustrates an embodiment of the present invention in which a large roller 12 is used in combination with moving belt 14 which contains or is coated with the sorbent material. Roller 12 and belt 14 define the sorption zone A and belt 14 and housing 16 define the desorption zone B. Small rollers 18 maintain the belt 14 in engagement with large roller 12 and guide rollers 20 keep the belt 14 positioned properly.

Figure 3:
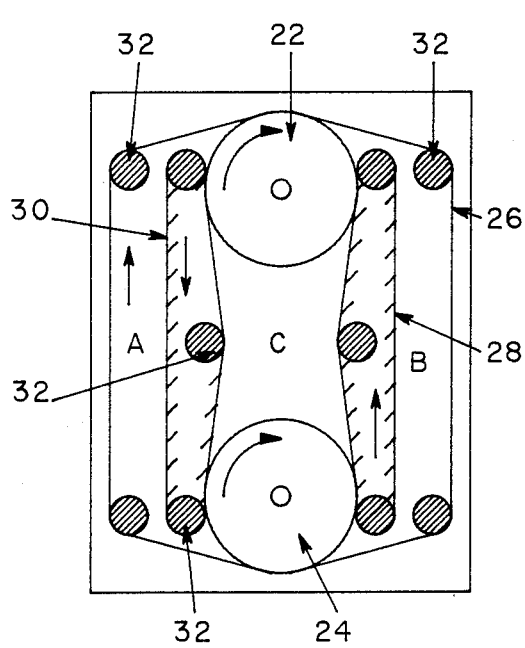
FIG. 3 is another cross section which illustrates a combination of two rollers and two moving belts.

FIG. 3 illustrates a different embodiment of the invention which utilizes large rollers 22 and 24, outer moving belt 26, and inner moving belts 28 and 30. A series of guide rollers 32 are used to maintain the engagement between outer belt 26 and inner belts 28 and 30 and also between inner belts 28 and 30 and large rollers 22 and 24. This apparatus defines three different zones. Zone A is defined by outer belt 26 and inner belt 30. Zone B is defined by outer belt 26 and inner belt 28. Zone C is defined by rollers 22 and 24 and inner belts 28 and 30. It is possible to use more than one sorbent with different selectivities and the sorbent material can be on the rollers or the belts or a combination thereof. One particular use for this device would be to absorb a component from both zone A and zone B and have it desorbed in zone C. Another use for this would be to absorb a component from zone C and have it desorbed in zones A and B which can be of different composition.

Figure 4:
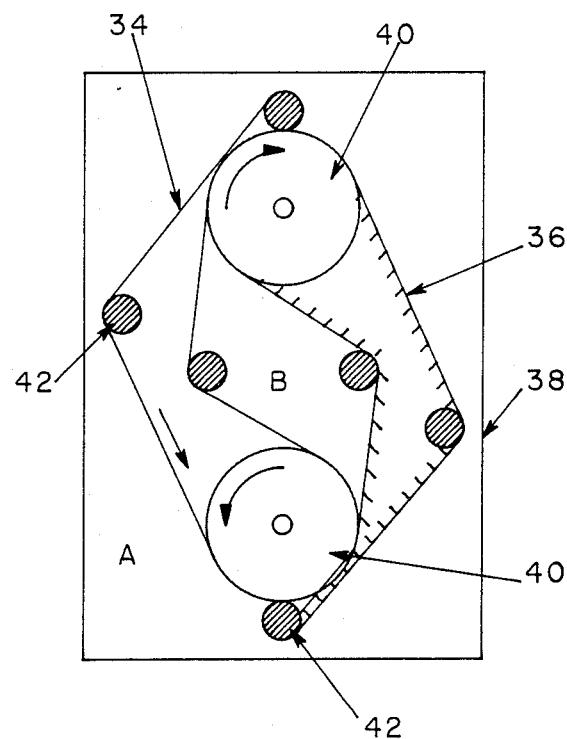
FIG. 4 is a cross section which illustrates the use of two moving belts, at least one of which is coated with the sorbent material to define the boundary between the sorption and desorption zones.

FIG. 4 illustrates an embodiment of the invention in which two moving belts 34 and 36 are used to define sorption and desorption zones A and B in combination with the housing 38. Large rollers 40 provide the means for moving the belts and guide rollers 42 maintain the belts in engagement with each other to separate the two zones. Either of the belts may contain or be coated with the sorbent material.

I claim:

1. A continuous process for separating components of a fluid mixture which comprises:
   a. Forming at least one sorption zone and at least one desorption zone in a separator comprising at least one roller, at least one belt, or a combination of at least one roller and one belt, at least one of the belts and rollers having sorbent material thereon in engagement so that the sorbent material forms a boundary seal between the sorption and desorption zones, said sorption material continuously moving back and forth between the sorption and desorption zones,
   b. Causing a fluid mixture to flow into the sorption zone wherein the conditions are such to promote sorption of at least one of the components of the mixture by a sorbent material, and
   c. Creating conditions in the desorption zone such that the sorbed component will be desorbed when sorbent material containing the sorbed component moves into the desorption zone.

2. The process of claim 1 wherein the desorbed component forms a part of a second fluid mixture which is present in the desorption zone.

3. The process of claim 2 wherein the desorption zone is a reaction zone and the rate of reaction is controlled by the amount of desorbed component which enters the desorption zone.

4. A continuous process for separating components of a fluid mixture which components:
   a. Forming at least one sorption zone and at least one desorption zone in a separator comprising at least two moving belts, at least one of the belts having sorbent material thereon in engagement so that the sorbent material forms a boundary seal between the sorption and desorption zones, said sorption material continuously moving back and forth between the sorption and desorption zones,
   b. Causing a fluid mixture to flow into the sorption zone wherein the conditions are such to promote sorption of one of the components of the mixture by a sorbent material, and
   c. Creating conditions in the desorption zone such that the sorbed component will be desorbed when sorbent material containing the sorbed component moves into the desorption zone.

5. The process of claim 4 wherein the desorbed component forms a part of a second fluid mixture which is present in the desorption zone.

6. The process of claim 5 wherein the desorption zone is a reaction zone and the rate of reaction is controlled by the amount of desorbed component which enters the desorption zone.

* * * * *